United States Patent
Bories et al.

(10) Patent No.: US 10,577,541 B2
(45) Date of Patent: Mar. 3, 2020

(54) CATALYTIC CRACKING METHOD FOR TREATING A FRACTION HAVING A LOW AMOUNT OF CONRADSON CARBON

(75) Inventors: Marc Bories, Saint Jouin de Bruneval (FR); Patrick Leroy, Saint Vigor d'Ymonville (FR); Eusebius Gbordzoe, Houston, TX (US)

(73) Assignee: Total Raffinage France, Courbevoie (FR)

( * ) Notice: Subject to any disclaimer, the term of this patent is extended or adjusted under 35 U.S.C. 154(b) by 374 days.

(21) Appl. No.: 14/129,786

(22) PCT Filed: Jun. 29, 2012

(86) PCT No.: PCT/FR2012/051505
§ 371 (c)(1),
(2), (4) Date: Mar. 27, 2014

(87) PCT Pub. No.: WO2013/001245
PCT Pub. Date: Jan. 3, 2013

(65) Prior Publication Data
US 2014/0221707 A1 Aug. 7, 2014

Related U.S. Application Data

(60) Provisional application No. 61/521,101, filed on Aug. 8, 2011.

(30) Foreign Application Priority Data

Jun. 30, 2011 (FR) .................................... 11 55852

(51) Int. Cl.
C10G 11/18 (2006.01)
C10G 11/00 (2006.01)
(Continued)

(52) U.S. Cl.
CPC .............. *C10G 11/182* (2013.01); *B01J 8/24* (2013.01); *B01J 38/02* (2013.01); *B01J 38/30* (2013.01);
(Continued)

(58) Field of Classification Search
CPC ................................ C10G 11/182; C07C 4/06
(Continued)

(56) References Cited

U.S. PATENT DOCUMENTS 2,902,432 A 9/1959 Codet et al.
3,092,568 A 6/1963 Atteridg
(Continued)

FOREIGN PATENT DOCUMENTS

CN 1763150 A 4/2006
EP 719850 A1 7/1996
(Continued)

OTHER PUBLICATIONS

Khadim et al., Determination of hydrogen and carbon contents in crude oil and petroleum fractions by NMR spectroscopy, 2003, The Arabian journal for science and engineering, vol. 27, No. 2A, pp. 147-162.*

(Continued)

*Primary Examiner* — Youngsul Jeong
(74) *Attorney, Agent, or Firm* — Albert Shung

(57) ABSTRACT

The present invention discloses a process for the catalytic cracking of a weakly coking feedstock having a Conradson carbon residue of 0.1% by weight and a hydrogen content of greater than 12.7% by weight, comprising at least a feedstock cracking zone, a zone for separating/stripping the effluents from the coked catalyst particles and a zone for regenerating said particles, characterized in that at least a solid carbon material in the fluidized state, having a carbon content equal to or greater than 80% by weight, is injected upstream of and/or during the catalyst regeneration step into a dense bed of coked catalyst.

15 Claims, 1 Drawing Sheet

(51) Int. Cl.
*C07C 4/06* (2006.01)
*B01J 38/30* (2006.01)
*B01J 38/02* (2006.01)
*B01J 8/24* (2006.01)

(52) U.S. Cl.
CPC .............. *C07C 4/06* (2013.01); *C10G 11/187* (2013.01); *C07C 2523/22* (2013.01); *C07C 2523/755* (2013.01); *C10G 2300/1014* (2013.01); *C10G 2300/301* (2013.01); *C10G 2300/708* (2013.01); *Y02P 30/20* (2015.11)

(58) Field of Classification Search
USPC ....................................................... 208/113
See application file for complete search history.

(56) References Cited

U.S. PATENT DOCUMENTS

| | | | |
|---|---|---|---|
| 3,692,667 A | | 9/1972 | McKinney et al. |
| 4,436,613 A | * | 3/1984 | Sayles .................. C10G 11/182 208/155 |
| 4,828,680 A | * | 5/1989 | Green .................... C10G 11/18 208/120.2 |
| 4,875,994 A | | 10/1989 | Haddad et al. |
| 4,980,050 A | | 12/1990 | Huh et al. |
| 7,022,221 B1 | | 4/2006 | Hedrick |
| 7,077,997 B1 | | 7/2006 | Sandacz |
| 2001/0025806 A1 | | 10/2001 | Steffens et al. |
| 2008/0035527 A1 | | 2/2008 | Eng et al. |

FOREIGN PATENT DOCUMENTS

| | | | | |
|---|---|---|---|---|
| WO | 0035575 A1 | | 6/2000 | |
| WO | WO0035575 | * | 6/2000 | ................ B01J 8/34 |
| WO | 2007094771 A1 | | 8/2007 | |

OTHER PUBLICATIONS

International Search Report issued in PCT/FR2012/051505 dated Dec. 6, 2012 (6 pages).

"Fluid Catalytic Cracking Handbook", second edition (2000) by Reza Sadeghbeigi, published by Gulf Professional Publishing.

Explanatory Dictionary by T.F. Efremova, Explanatory Dictionary of the Russian Language, edited by D.N. Ushakov et al.

Eurasian Office Action issued in Application No. 201400051, dated Jan. 14, 2016, 8 pages.

* cited by examiner

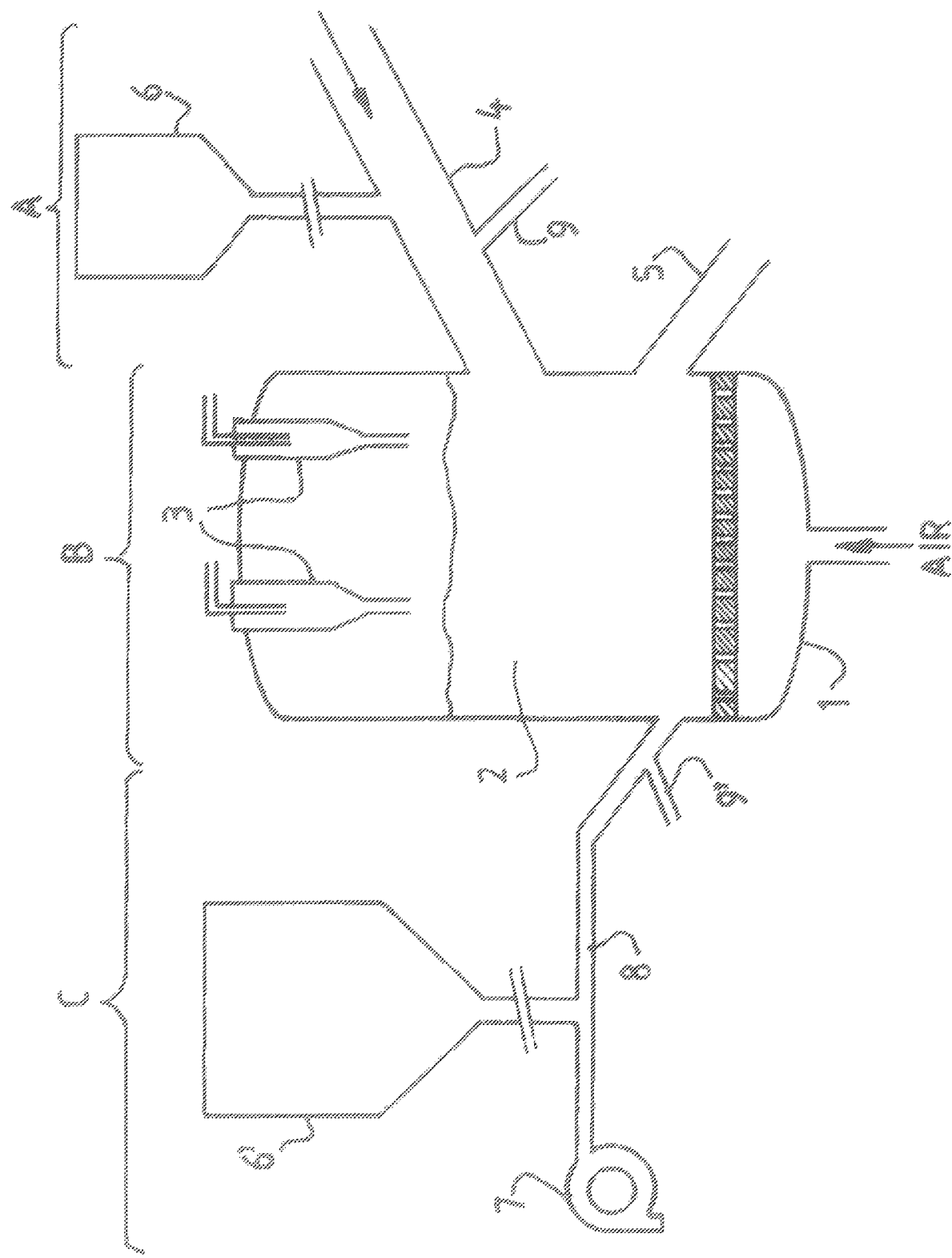

CATALYTIC CRACKING METHOD FOR TREATING A FRACTION HAVING A LOW AMOUNT OF CONRADSON CARBON

CROSS-REFERENCE TO RELATED APPLICATIONS

This application claims the benefit of PCT/FR2012/051505, filed on Jun. 29, 2012, which claims priority from FR 1155852, filed on Jun. 30, 2011, and U.S. Provisional Application No. 61/521,101, filed on Aug. 8, 2011.

The field of the present invention is that of the catalytic cracking of petroleum fractions, more particularly fractions which have a low Conradson carbon residue and a high hydrogen content and which, consequently, make it difficult to obtain the heat balance of the FCC (fluid catalytic cracking) unit.

In an FCC unit, the heat balance is mainly provided by the combustion of coke deposited on the catalyst during the cracking step. The heat of combustion allows the catalyst to be heated to temperatures typically ranging from 670 to 750° C. The catalyst releases the heat stored in the regenerator into the reactor to vaporise the feedstock to be cracked, which is injected in liquid form, and to provide the energy necessary for cracking the feedstock via overall endothermic reactions. An FCC unit is said to be a thermally balanced unit since the energy produced in the regenerator is therefore transported to and then consumed in the reactor by circulation of the catalyst. Typically, the catalyst enters the regeneration zone with a coke content (defined as the ratio of the mass of coke to the mass of catalyst expressed as a percentage by weight) of between 0.5 and 1.45% by weight and leaves said zone with a coke content of between 0.1 and 0.5% by weight for regenerators operating in partial combustion mode or between 0.1 and 0.05% by weight, or even less than 0.01% by weight, for regenerators operating in complete combustion mode. When a regenerator is operating in partial combustion mode or in complete combustion mode, the combustion is performed with a gas containing oxygen.

In complete-combustion regeneration, all of the coke is burnt (typical CO (carbon monoxide) content in the flue gas close to zero) whereas in partial combustion mode the combustion of the coke produces CO with a content of a few percent by volume, typically 0.5 to 10% by volume, depending on the air throughput and the degree of completeness of the combustion in the case of incomplete combustion.

The Conradson carbon residue (or CCR) of the feedstock is defined by the ASTM D 482 standard and represents, for those skilled in the art, a measure of the amount of coke that the feedstock may produce during the catalytic cracking reaction that takes place in the main reactor of the unit. Depending on the Conradson carbon residue of the feedstock, it is possible to size the unit for a coke yield corresponding to the cracking of the feedstock so as to meet the heat balance of the unit that will control the correct operation thereof.

Conventional heavy fractions treated in an FCC unit generally have Conradson carbon values lying in the range from 0.2 to 10% by weight.

The fractions treated in an FCC unit according to the present invention may have a Conradson carbon residue equal to or less than 0.1% by weight and a hydrogen content equal to or greater than 12.7% by weight.

EXAMINATION OF THE PRIOR ART

To equilibrate the heat balance, those skilled in the art know to push the combustion in the regenerator by injecting thereinto more air for a given amount of coke, i.e. to reduce the volume percentage of carbon monoxide (CO) in the flue gas, which contributes to increasing the temperature in the said regenerator and necessarily helps to meet the heat balance of the unit.

When this situation is not sufficient or possible, it is known in the prior art to recycle into the regenerator a fuel in liquid form in a burner generally placed in the dense phase of the catalyst bed. This fuel, often called by those skilled in the art "high-viscosity fuel" or "torch oil", generally contains one or more predominantly aromatic "heavy" fractions having an initial boiling point above 360° C. These fractions may come from the FCC unit or any other conversion unit in the refinery, such as a coker, a visbreaker, etc. It is also possible to use other types of fuel, such as fuel oil No. 2 or else fuel oils not meeting the specifications required for commercializing them. This injection of fuel into the regenerator is a common practice in the start-up phases of the unit, but may be a source of problems when used continually. This is because, since the temperatures in the regenerator are around 650° C. to 750° C., a portion of the recycle vaporizes, forming cracked gases that are not entirely oxidised in the dense phase of the regenerator and will therefore be found in the dilute phase of the regenerator where they thus run the risk of creating hot spots that may be damaging to the proper operation of the regenerator. This phenomenon, often called "afterburning" or "post-combustion", may be defined as further combustion at an undesired point in the regenerator, for example in the dilute phase where the solid catalyst is present in a smaller amount, or at the inlet of or inside one of the cyclones also present in the enclosure of the regenerator, or else in the combustion gas discharge lines. This term "afterburning", well accepted and practiced by those skilled in the art, will be used in the rest of the text.

Moreover, this recycle stream runs the risk of burning in the catalyst bed, locally forming a high-temperature flame front. This flame front generates hot spots with locally high temperatures within the catalyst bed. Since steam also forms when these hydrocarbons are burnt, such local high temperatures combined with the presence of steam weaken the active part of the catalyst (zeolite) and thus deactivate its cracking function. It is referred to as hydrothermal catalyst deactivation. Thus, the lighter the recycle fraction, the richer it is in hydrogen and the more it generates steam by combustion in the regenerator. All these undesirable phenomena described above are obviously exacerbated as the amount of liquid fuel recycled into the regenerator, to maintain the heat balance of the FCC unit, increases.

In such a context, that is to say with a feedstock that produces little coke during the cracking operation, and to avoid continuously injecting liquid hydrocarbons (or torch oil), which are responsible inter alia for the afterburning and degradation of the catalyst, into the regenerator, refiners have often chosen to install a feedstock preheat furnace upstream of the cracking reactor using a fuel having a high hydrogen content. Adding such a preheat furnace therefore makes it possible to supply the heat, which will be added to that produced by the combustion of the coke, to the catalyst in the regenerator and thus equilibrates the heat balance of the unit. The supply of heat by the preheat furnace will be greater the lesser the amount of heat supplied by the regenerator. However, there is a maximum preheat temperature limit for the feedstock, which corresponds to the cracking onset temperature thereof. It should be pointed out that installing such preheat furnaces is expensive, not only in terms of purchase cost but also operating cost because of the external energy consumed.

In one of its first objectives, the present invention aims to provide a process for the catalytic cracking of a weakly coking feedstock, having a Conradson carbon residue equal to or less than 0.1% by weight and/or a hydrogen content equal to or greater than 12.7% by weight, which comprises the injection in divided state, into the dense fluidized bed of the regenerator, consisting of relatively coked catalyst particles, of a coke-rich material making it possible to increase the amount of coke to be burnt off in the regenerator without promoting the formation of hot spots (afterburning) around the catalyst particles so as to prevent them from being deactivated.

It is known to inject coke-type compounds into cracking reactors and to blend them with the regenerated catalyst in one or more stages, the objective being to promote demetallization of heavy feedstocks, heavy metals of the nickel and vanadium type being trapped in the pores of said coke. Such applications are claimed in U.S. Pat. Nos. 3,092,568 and 4,875,994.

In U.S. Pat. No. 4,828,680, coke in powder form, dispersed in fresh catalyst, is injected into the regenerator as catalyst make-up, the coke particles having a size comparable to that of the fresh cracking catalyst. The problem encountered in this type of coke injection is that of how to disperse the catalyst into the coke mixture homogeneously before it is injected into the regenerator.

A second objective of the invention is to ensure that the dispersion of the coke within the coked catalyst particles or on the catalyst particles undergoing regeneration is homogeneous.

BRIEF DESCRIPTION OF THE INVENTION

The present invention applies both to FCC units using a reactor operating in upflow mode (called a "riser" reactor) and to units using a reactor operating in downflow mode (called a "downer" reactor).

The present invention also applies to FCC units operating with a single reactor (in upflow mode or downflow mode) and to FCC units operating with two or more reactors. In general, when the FCC units operate with two reactors—a main reactor and a secondary reactor—they operate in maximum gasoline or maximum GPL mode, or else in maximum distillate or LCO (light cycle oil) mode, these reactors are riser reactors, but a unit operating with two downer reactors or with one riser reactor and one downer reactor would not be outside the scope of the present invention.

For this purpose, the invention relates to a process for the catalytic cracking of a weakly coking feedstock having a Conradson carbon residue equal to or less than 0.1% by weight and a hydrogen content equal to or greater than 12.7% by weight, said process being implemented in a unit comprising at least a feedstock cracking zone, a zone for separating/stripping the effluents from the coked catalyst particles and a zone for regenerating said particles, characterized in that at least a solid carbon material in the fluidized state, having a Conradson carbon residue equal to or greater than 10% by weight, is injected upstream of and/or during the catalyst regeneration step into a dense bed of coked catalyst in the regeneration zone.

According to the invention, the process is such that:
(a) at least one solid carbon material in the fluidised state, having a carbon content equal to or greater than 80% by weight, is dispersed on the coked catalyst particles:
  (i) upstream of the regenerating zone and downstream of the separating/stripping zone, and/or
  (ii) in the zone for regenerating catalyst within the coked catalyst particles of a dense bed.
(b) the amount of solid carbon material in the fluidized state dispersed within the coked catalyst particles of the dense bed is adjusted so as to deliver an additional amount of coke $Q_C$ to the catalyst so as to satisfy the following equation (I):

$$Q_c = Q_t - Q_i \quad (I),$$

in which $Q_i$ is the initial coke content of the coked catalyst after the feedstock has been cracked and a or delta coke is the coke content necessary for maintaining the temperature of the regenerated catalyst and therefore the heat balance of the process,
(c) the mixture of coked catalyst particles and solid carbon material is burnt in the regeneration zone to produce a regenerated catalyst having a reduced content of carbon material,
(d) the regenerated catalyst is mixed with the weakly coking feedstock in the cracking zone to produce the coked catalyst particles and the effluents,
(e) the coked catalyst particles are separated from the effluents in the separating/stripping zone, then the coked catalyst particles are sent back to the regeneration zone.

Advantageously, all of the added carbon material may be burnt within the regeneration zone. Indeed, if the added carbon material were not completely burnt, it would result in formation of coke dust which would be partly recovered in the cyclones of the disengager of the separating/stripping zone and partly recovered in the cyclones of the regeneration zone, where this coke dust is responsible of afterburning and accelerated degradation of the cyclones.

In the present application, the terms upstream and downstream are relative to the envisaged circulation of the catalyst in the regenerating zone.

The carbon material may be fluidized, by any means, in a liquid or gaseous effluent not amalgamating with the carbone material, preferably air.

According to the invention, the amount of solid carbon material in the fluidized state dispersed within the coked catalyst particles of the dense bed is adjusted so as to deliver an additional amount of coke $Q_C$ to the catalyst so as to satisfy the following equation (I):

$$Q_c = Q_t - Q_i \quad (I),$$

in which $Q_i$ is the initial coke content of the coked catalyst after the feedstock has been cracked and $Q_t$ or delta coke is the coke content necessary for maintaining the temperature of the regenerated catalyst and therefore the heat balance of the process.

In particular, $Q_t$ may be chosen to be from 0.5 to 1% by weight when the regeneration zone comprises only a single step and from 0.8 to 1.45% by weight for a partial combustion in the first stage of a regeneration zone of a multistage regenerator having at least two regeneration steps.

The carbon material may be chosen from the following: coke resulting from the coking of coal; coke from cokers for hydrocarbon effluents having a boiling point above 350° C. chosen from heavy effluent fractions coming from the main cracking reaction, HCOs (heavy cycle oils) with a distillation range typically between 360 and 440° C. and slurries with a distillation range above 360° C. (denoted by 360°+); biomass residues coming from the conversion of wood and/or cellulose; powdered coal dissolved in a fluid hydrocarbon and/or injected by blowing or spraying; asphalt-rich fractions coming from deasphalting units; non-utilizable waxes coming from the liquefaction of coal by an indirect (GTL) process or from a Fischer-Tropsch process for converting gas into hydrocarbons; and a mixture of said fractions.

The feedstock injected into the cracking zone may be chosen from the group comprising the following: purges or bleeds from a hydrocracking unit; feedstocks based on vacuum-distilled gas-oil fractions having a boiling point above 350° C. and having hydrogen contents equal to or greater than 12.7% by weight; vegetable oils; and hydrocarbons having a boiling point below 160° C., these feedstocks being cracked individually or as a mixture in the cracking zone of the process.

The solid carbon material in the fluidized state containing the coked material may be injected into the dense phase of at least one step of the regeneration zone when this is a multistage zone.

The Dispersion of solid carbon material in the fluidized state may be obtained by means for dispersing said material over the entire section of the regeneration zone so that the ratio of the distribution of the catalyst particles to that of the carbon material within the regeneration zone is close to 1. In other words, the proportion of catalyst particles over carbon material particles is constant in any point of the section of the regeneration zone.

For this purpose, the regeneration zone may be equipped with at least one structured packing, placed upstream and/or downstream of means for dispersing the carbon material relative to the envisaged circulation of the catalyst in said regenerator, whatever the dispersing means. Advantageously, this structured packing will be placed upstream from the means for dispersing the carbon material.

The regeneration zone may be equipped with at least one structured packing for dispersing the coked catalyst particles and the homogeneous dispersion of solid carbon material in the fluidized state may be carried out countercurrently of the catalyst circulation, downstream of said structured packing, said packing covering all or part of the section of said regeneration zone.

For example, the homogeneous dispersion may be carried out in the presence of at least one packing placed in the dense phase of a first stage of the regeneration zone in the case of a multistage regeneration zone.

The solid carbon material in the fluidized state may be dispersed over all or part of the height of each dense bed of the regeneration zone, each dispersion taking place after the fluidized bed has been homogenized, this bed being optionally equipped with at least one structured packing.

The invention also relates to a plant for implementing the process according to the invention, comprising at least a main reactor and possibly at least a secondary reactor, at least a disengager/stripper, and a single-stage or multistage regenerator, characterized in that it includes means for homogeneously dispersing a carbon material in the divided state over coked catalyst particles coming from the disengager/stripper, these homogeneously dispersing means being located upstream of the regenerator and/or in the regenerator itself. According to the invention, the regenerator is further equipped with at least one structured packing, placed upstream and/or downstream of means for dispersing the carbon material relatively to the envisaged circulation of the catalyst within the regenerator.

The means for dispersing the carbon material may be placed in a line connecting the stripper to the regenerator and conveying the stripped coked catalyst to said regenerator.

The means for dispersing the carbon material may also be placed in a dense part of the fluidized bed in the regenerator.

Optionally, means for dispersing the carbon material may be placed at the two locations described above.

When the dispersing means are placed in a line connecting the stripper to the regenerator and conveying the stripped coked catalyst to said regenerator, they may comprise a hopper for storing carbon material preground to the desired particle size. It if for example possible to use the same hopper for storing and injecting both the catalyst, whether fresh or equilibrium (issued from the cracking zone) catalyst, and the carbon material particles.

When the dispersing means are placed in the regenerator, they may be chosen from means capable of dispersing gas/solid mixtures in a dense bed. They are preferably open tubes and/or rakes formed from several parallel tubes opening into the dense bed, these tubes being connected to a manifold tube.

The regenerator may be equipped with at least one structured packing, placed upstream and/or downstream of the means for dispersing the carbon material relative to the envisaged circulation of the catalyst in said regenerator.

In particular, the regenerator may be equipped with at least one structured packing, placed upstream of the means for dispersing the carbon material relative to the envisaged circulation of the catalyst in said regenerator within the dense fluidized bed of the first regeneration stage.

These packings are for example formed by interlacing plates, strips or fins constituting a screen, this screen occupying less than 10% of the area of the cross section of the vessel in which it is placed, covering, in projection on said section, the entire surface thereof.

DETAILED DESCRIPTION OF THE INVENTION

The feedstocks that an FCC unit according to the present invention can treat are feedstocks having a Conradson carbon residue equal to or less than 0.1% by weight and having a hydrogen content equal to or greater than 12.7% by weight.

The present invention may be described as a process for the catalytic cracking of a weakly coking feedstock having a Conradson carbon residue equal to or less than 0.1% by weight and a hydrogen content equal to or greater than 12.7% by weight, this process being implemented in a unit comprising at least a feedstock cracking zone, a zone for separating/stripping the effluents from the coked catalyst particles and a zone for regenerating said particles, the feature of the process being that at least a solid carbon material in the fluidized state, the carbon content of which is equal to or greater than 80% by weight, is injected upstream of and/or during the catalyst regeneration step, into a dense fluidized bed of coked catalyst particles.

According to the invention, the process is such that:
(a) at least one solid carbon material in the fluidised state, having a carbon content equal to or greater than 80% by weight, is dispersed on the coked catalyst particles:
  (i) upstream of the regenerating zone and downstream of the separating/stripping zone, and/or
  (ii) in the zone for regenerating catalyst within the coked catalyst particles of a dense bed.
(b) the amount of solid carbon material in the fluidized state dispersed within the coked catalyst particles of the dense bed is adjusted so as to deliver an additional amount of coke $Q_C$ to the catalyst so as to satisfy the following equation (I):

$$Q_c = Q_r - Q_i \qquad (I),$$

in which $Q_i$ is the initial coke content of the coked catalyst after the feedstock has been cracked and $Q_t$ or delta coke is the coke content necessary for maintaining the temperature of the regenerated catalyst and therefore the heat balance of the process, (c) the mixture of coked catalyst particles and solid carbon material is burnt in the regeneration zone to produce a regenerated catalyst having a reduced content of carbon material, (d) the regenerated catalyst is mixed with the weakly coking feedstock in the cracking zone to produce the coked catalyst particles and the effluents, (e) the coked catalyst particles are separated from the effluents in the separating/stripping zone, then the coked catalyst particles are sent back to the regeneration zone.

To divide, or even fluidize, the particles of solid carbon material in a liquid or gaseous effluent, any means similar to that used in particular for fluidizing catalyst may be used, said effluent having to keep the particles of said material divided and non-amalgamated. Preferably, air is used as effluent for fluidizing this solid carbon material in the divided state.

The term "regeneration zone" is understood to mean a zone in which a regeneration of the coked catalyst is performed which takes place in one or more steps, generally two steps, in one and the same vessel comprising one or more stages and/or in different regeneration vessels comprising one or more steps in one or more stages.

The cracking zone, dedicated to the cracking of the feedstock, comprises at least one reactor, in particular at least one main reactor and at least one secondary reactor.

The separating/stripping zone is dedicated to separating and stripping the coked catalyst particles from the effluents issued from the cracking of the feedstock. This separating/stripping zone comprises at least one disengager and at least one stripper.

A weakly coking feedstock is a feedstock that will produce a weakly coked catalyst at the outlet of the cracking reactor, the amount of coke not being high enough to maintain the heat balance of the catalytic cracking unit in which it is used, typically said amount is less than 0.4% by weight. Specifically, the regeneration of the catalyst, by burning off the coke, releases heat that should be recovered in sufficient amount by the catalyst so that the latter supplies, on the one hand, energy sufficient to vaporise almost completely the feedstock injected in liquid form into the reactor and supplies, on the other hand, sufficient energy to the generally endothermic cracking reactions so as to maintain a reaction temperature at the outlet of said reactor which is generally between 480 and 650° C. depending on the desired conversion objectives and configurations.

To enable said carbon material to be dispersed, the present invention uses any means for homogeneously dispersing a solid material, such as those currently used for injecting fresh catalyst into a dense catalyst bed. For better compatibility between coked catalyst particles and particles of the carbon material, measures will be taken to ensure that the particle size of the carbon material is best suited for making it possible not only to obtain good fluidization behaviour but also to limit elutriation of the particles of highly carbonaceous material in the dilute phase above the dense bed. For this purpose, the particle size of the added carbon material(s) may advantageously be roughly identical to the particle size of the catalyst particles. The term "roughly identical" means an identical size with a variation of ±10%.

The advantage of the present invention is essentially that the amount of coke in the regenerator is increased, thus making it possible to compensate for the small amount of coke formed by the feedstock in the cracking reactor. This increase in the amount of coke to be burnt off in the regenerator, having a very low hydrogen content, has the effect of increasing the heat resulting from the combustion of the coke and consequently of increasing the temperature of the resulting regenerated catalyst particles that will be recycled into the main reactor in a single-reactor configuration and to the main and secondary reactors in a two-reactor configuration. The final advantage is to make it possible for the amount of coke needed for thermal equilibrium of the unit to be adjusted as required and thus to ensure that said unit operates efficiently.

For efficient operation of the FCC unit fed with a weakly coking feedstock, the amount of coke ($Q_t$) present on the catalyst entering the regeneration zone, necessary for equilibrating the heat balance, will correspond to the sum of the initial amount of coke ($Q_i$) supplied by the cracking of the feedstock on the catalyst (in the main reactor or in the two or more reactors of the FCC unit) and of the amount of coke ($Q_c$) supplied by fluidizing the carbon material on the coked catalyst after the feedstock has been cracked. In general, $Q_t$, namely the amount of coke entering the regenerator, typical for a balanced heat balance, is maintained between 0.5 and 1% by weight when the combustion is in the case of a single-step regeneration zone and between 0.8 and 1.45% by weight for partial combustion in the first step of a regeneration zone of a multistage regenerator comprising at least two regeneration steps.

In the context of the present invention, the amount of carbon material dispersed within the coked catalyst particles is adjusted so as to deliver an additional amount of coke $Q_C$ to the catalyst so as to satisfy the following equation (I):

$$Q_c = Q_t - Q_i \qquad (I),$$

in which $Q_i$ is the initial coke content of the coked catalyst after the feedstock has been cracked and $Q_t$ or delta coke is the coke content necessary for maintaining the temperature of the regenerated catalyst and therefore the heat balance of the process.

To implement the invention, the carbon material having a carbon content equal to or greater than 80% by weight may be chosen among:

coke having a hydrogen content equal to or less than 10% by weight, this coke resulting from: the coking of coal; cokers for hydrocarbon effluents having a boiling point above 350° C. chosen from heavy effluent fractions coming from a cracking reaction, HCOs (heavy cycle oils) with a distillation range typically between 360 and 440° C. and slurries with a distillation range above 360° C. (denoted by 360°+);

biomass residues coming from the conversion of wood and/or cellulose;

powdered coal dissolved in a fluid hydrocarbon and/or injected by blowing or spraying;

asphalt-rich fractions coming from deasphalting units;

non-utilizable waxes coming from the liquefaction of coal by an indirect (GTL) process or from a Fischer-Tropsch process for converting gas into hydrocarbons; or a mixture of said fractions.

Among the weakly coking feedstocks that the present invention can treat may be found the following:

purges from a hydrocracker unit, called bleeds, having a hydrogen content equal to or greater than 12.7% by weight;

severely pretreated VGO (vacuum gas oil, resulting from the vacuum distillation of atmospheric distillation residues) feedstocks, generally having a boiling point above 350° C. and having hydrogen contents equal to or greater than 12.7% by weight;

vegetable oils; and hydrocarbons having a distillation point of 160° C. or below, such as gasolines, or even certain liquefied gas molecules such as butane, coming from distillation and/or conversion units.

These feedstocks may be cracked individually or as a mixture in the main reactor of the catalytic cracking unit.

The present invention involves the production of effluents such as, for example, petrol (gasoline) and LPG (liquefied petroleum gas) from a weakly coking feedstock, such as one of those mentioned above, by fluid catalytic cracking (FCC) in a corresponding unit that has at least one main reactor operating in upflow mode (riser reactor) or in downflow mode (downer reactor), the coked catalyst leaving the reactor being injected into a separating/stripping zone at the outlet of which the coked catalyst is recovered and sent into the regenerator of the unit. The regenerator may be a single-stage or multistage regenerator. In the case of a single-stage reactor, this comprises at least one fluidized bed of coked catalyst particles, in which the combustion of the coke takes place, these being distributed according to their respective average density, including at least one dense-phase bed in which most of the combustion takes place, and at least one dilute-phase bed in which the completely or partly decoked catalyst particles separate from the gaseous effluents resulting from the combustion. It is in that part of the dense fluidized bed in which the combustion reaction is the most complete that the catalyst may reach the intended temperature before it is recycled to the main reactor. It is therefore into the dense bed that the carbon material is injected in fluidized form.

In order for the carbon material injected in fluidized form to be homogeneously blended within the catalyst particles, it is necessary to disperse the particles of carbon material over the entire cross section of the bed by suitable dispersing means so that the ratio of the distribution of the catalyst particles to that of the particles of carbon material is close to 1. One of the means for achieving such a ratio is to homogenise the dense phase of the fluidized bed by the insertion of structured packings that improve the dispersion of the coked catalyst particles upstream of the dispersing of the particles of carbon material, this dispersing operation being carried out by any means. The structured packings may cover all or part of the cross section of the regenerator and over at least a portion of the height thereof. Thus, it would be conceivable to inject, possibly in a staged manner, the carbon material over all or part of the height of the dense bed, each dispersion of carbon material taking place after the fluidized bed has been homogenised by means of a structured packing.

By using structured packings it is possible to provide a continuous catalyst stream of homogeneous density. In a preferred embodiment, these packings occupy less than 10% of the area of the flow cross section in the vessel in which they are placed, although in projection on said vessel they occupy the entire area thereof.

One of the advantages associated with using such packings is that they make it easier for homogenisation and combustion of the carbon material injected into the dense phase, thereby limiting the occurrence of hot spots in the fluidized bed. Another advantage is that the entrainment of incompletely burnt carbonaceous particles into the gases output from the regenerator is limited.

When a multistage regenerator comprising at least two regeneration stages is operated, the first stage serves for the partial combustion of the coke present on the catalyst particles coming from the reactor, this partial combustion leading to the formation of CO and most particularly steam coming from the hydrogen atoms present. Since the combustion is partial, even if there is steam formation close to the catalyst particles, the reaction temperature is lower and the probability of reducing the activity of the catalyst particles is lower. The addition of carbon material having a hydrogen content of less than 10% by weight will not disturb the partial combustion if the amount of carbon material relative to that of the coked catalyst particles is equivalent, that is to say with a mass ratio close to 1. As regards the second stage, this behaves as a single-stage regenerator in complete combustion mode.

In the context of the present invention, it is possible to inject carbon material in the fluidized state both into the first regeneration stage and into the second regeneration stage, but always into the dense phase of the fluidized bed contained in these stages. This injection could be improved by inserting structured packings as described above, upstream of the dispersing of the carbon material in said bed. Moreover, it is preferable to inject carbon material into the first stage of the regenerator (the one having two regeneration stages) in order to have more time to finalise the combustion of the carbon material particles.

However, the injection of coke coming in particular from cokers poses other problems in the operation of the unit. Coke such as coke from a coker, also called "petcoke", generally contains many heavy metals such as nickel and vanadium that are poisons for the catalytic activity of the catalyst used in FCC units, but also contains sulphur and nitrogen, the amount of which must be limited. It is known that the amount of heavy metals that can be tolerated in the catalyst of an FCC unit is at most 10 000 ppm, preferably less than 6500 ppm for a two-stage regenerator and from 5000 to 7000 ppm for a single-stage regenerator. To control the amount of heavy metals accumulated in the catalyst, a complement of fresh or equilibrium catalyst, called "flush cat" by those skilled in the art, is injected into the regenerator so as to reduce the amount of metals circulating in the unit. The presence of nitrogen and sulphur in the coke injected into the regenerator will inevitably lead to the formation of undesirable polluting species in the flue gas leaving the regenerator, such as NOx and SOx. To limit the formation of these species during combustion of the coke, commercial additives, called "DeSOx" additives, known to those skilled in the art may be used. These additives, sold by all catalyst vendors, help to capture the $SO_2$ in the regenerator and transport it to the reaction zone where, in the presence of steam, the $SO_2$ is then released in the form of sulphurous acid ($H_2SO_3$), which will then be recovered in the cracked-gas scrubbing section. In the case of NOx, the preferred solution is of the SCR (selective catalytic reduction) or SNCR (selective non-catalytic reduction) type. Finally, mention should be made of flue gas scrubbers that can abate both NOx and SOx, and also catalyst particles. In all cases, it is necessary to carry out a technico-economic study so as to select the most appropriate flue gas treatment option in accordance with the discharge legislation.

Another subject of the present invention is a plant for implementing the invention, comprising the various vessels needed to implement a catalytic cracking process, that is to say at least a main reactor and possibly at least a secondary reactor, at least a disengager and a stripper and a single-stage or multistage regenerator, said plant including means for homogeneously dispersing a carbon material in the divided state on the coked catalyst particles upstream of the regenerator and/or in the regenerator itself. These homogeneous dispersing means are for example those used for injecting fresh catalyst into a dense catalyst bed.

These dispersing means may comprise a hopper for storing carbon material preground to the desired particle size. The carbon material particles are preferably maintained in the fluidized state by injecting air into the hopper. In the hopper an injection system serves to transport the carbon material particles to the regenerator using a carrier gas, typically air, the flow rate of which is adjusted by a restricting orifice, and enabling the amount of carbon material sent to the dense phase of the regenerator to be controlled. The system here is similar to that used for injecting fresh catalyst into any FCC unit, as known to those skilled in the art. It should be mentioned that, in many possible variants of the invention, it is possible to use the same hopper for storing and injecting both the catalyst, whether fresh or equilibrium catalyst, and the carbon material particles.

The dispersing means, when they are placed in the regenerator, may also be chosen among means capable of dispersing gas/solid mixtures in a dense bed. They are preferably open tubes and/or rakes formed from several parallel tubes opening into the dense bed, these tubes being connected to a manifold tube.

According to the invention, the regenerator is further equipped with at least one structured packing, placed upstream and/or downstream of the means for dispersing the carbon material relatively to the envisaged circulation of catalyst within the regenerator.

In a first embodiment of the plant, the carbon material dispersing means are placed in a line connecting the stripper to the regenerator and conveying the stripped coked catalyst to said regenerator. Advantageously, at least one structured packing may be placed in said line between the stripper and the regenerator, after the point of injection of the carbon material particles (relative to the envisaged circulation of catalyst in said regenerator), in order to ensure better homogenisation of the carbon material/catalyst blend.

In a second embodiment of the plant, the dispersing means are advantageously placed in part of the dense bed. The regenerator will be equipped with at least one structured packing, placed downstream and/or upstream of the carbon-material dispersing means with respect to the envisaged circulation of catalyst in said regenerator.

In a variant, several packings, each being associated with a carbon-material dispersing means, may come one after another with at least one packing associated with a dispersing means.

As packing elements, one or more of the structured packings described in the patents EP 719 850, U.S. Pat. Nos. 7,022,221, 7,077,997, WO 2007/094771, WO 00/35575 and CN 1 763 150 may be used. Here, in each of the envisaged packings, the stream of coked particles is aerated by making them follow preferential pathways obtained by interlacing plates, strips or fins constituting a screen. The cross section of this screen parallel to the cross section of the vessel containing it may occupy less than 10% of the area of the flow cross section of said vessel but, in projection on said section, it may cover the entire area thereof. Such interlacing is generally arranged in layers of the same type, enabling this aerating of the particles to be controlled.

Upstream of the dispersing means of the carbon material, the raw carbon material is finely ground and then screened, and only the particles having the required size, i.e. approximately the size of the fresh catalyst particles, are sent into a line into which a carrier gas, typically air, is injected, thereby entraining the divided solid into the devices for dispersing it in the coked catalyst.

The dimensioning of such a dispersing device follows the same design rules as those used by a person skilled in the art for pneumatically transporting a finely divided solid, such as the catalyst, from its storage hopper to its point of injection into a dense bed. Among the means capable of dispersing the gas/solid mixtures in a dense bed, it is preferable to use open tubes and/or rakes formed from several parallel tubes opening into the dense bed, these tubes being connected to a manifold tube.

Whatever the device for dispersing the carbon material in the dense bed, the regenerator may be operated in total or partial combustion mode, in presence of a gas containing oxygen. For operation in partial combustion mode, the injected air is not able to burn off all of the coke present in the regenerator, coming from both the coke on the coked catalyst particles and from the carbon material particles intentionally injected into the regenerator. In this case, coke particles will move towards the reaction zone. The advantage of such a situation is the ability to dilute the catalytic activity of the circulating catalyst mass and therefore to reduce the degree of conversion of the treated feedstock so as to maximise the production of distillate. Another advantage of this operation in partial combustion mode is that the heat balance is not significantly modified since the coke particles are at the temperature of the dense phase in the regenerator.

The invention will now be described with reference to the appended non-limiting drawings in which:

The FIGURE is a section through a regenerator equipped with a system for dispersing carbon material particles in a gaseous fluid up to the inlet of the dispersion device therein: two arrangements are possible, namely AB and BC, depending on whether the carbon material is injected into the line between the stripper and the regenerator or directly into the regenerator (for example via another line).

The FIGURE shows, in its main part B, a regenerator (1) containing a dense catalyst bed (2) equipped with two cyclones (3) for a final gas/solid separation before the $CO_2$-laden combustion gas is discharged. The regenerator (1) is equipped with an inlet (4) for the coked catalyst, with a line (5) for discharging the regenerated catalyst and, at the bottom, an air inlet. The regenerator (1) is coupled with a carbon material, for example coke, injection system in two possible configurations, AB and BC. These two systems for injecting the carbon material corresponding to the parts A and C are shown in the FIGURE. In each part A or C, the carbon material is ground in vessels (6 or 6') and then the carbon material, in the form of powder particles, is sent into a line (4) in the AB configuration or a line (8) in the BC configuration. In the latter configuration, the line (8) is equipped with an air blower (7) capable of keeping the injected carbon material particles in the fluidized state circulating up to the regenerator where the carbon material is blended with the dense bed of coked catalyst. The lines (4) and (8) are equipped with injectors (9) and (9') for injecting DeSox and DeNOx additives.

Examples are given below to illustrate the invention, but they should not be interpreted as limiting the invention.

EXAMPLE

This example shows the advantages of the present invention by comparing the efficiency in terms of product yield when weakly coking feedstocks are cracked in an FCC unit with and without recycle of coking fractions.

The production of coke in the coker was 250 t/h of the following composition: C=85.2 wt %; H=3.6 wt %; N=1 wt %; S=7.5 wt %; Ni=179 ppm (by weight); and V=565 ppm (by weight). The calorific value of the coke was assumed to be equal to 7.75 kcal/kg. This coke is the coked used in this example.

A base case may be distinguished in which there is no coke injection using an FCC unit having a single riser reactor with a capacity of 4800 tonnes per day, i.e. 200 tonnes per hour, and treating a corresponding hydrotreated VGO feedstock, the properties of which are given below.

TABLE 1

Properties of the hydrotreated VGO

| Feedstock | | Hydrotreated VGO |
|---|---|---|
| Density | g/cm$^3$ | 0.8610 |
| H$_2$ content | wt % | 13.7 |
| Sulphur content | ppm by weight | 330 |
| Nitrogen content | ppm by weight | 550 |
| CCR (Conradson carbon residue) | wt % | <0.1 |
| Ni content | ppm by weight | <2 |
| V content | ppm by weight | <2 |

Trials on a pilot plant have shown that this feedstock produced very little coke, about 3.3% for a reaction temperature of 525° C. and a C/O ratio of 8. On the basis of this pilot data, we carried out heat balance calculations under various operating cases of an industrial unit which, by definition, must close the heat balance thereof. The results of these calculations are given in Table 2 below. The heat balance calculations were carried out on the basis of the calculation formulae mentioned in the work: "Fluid Catalytic Cracking Handbook", second edition (2000) by Reza Sadeghbeigi, published by Gulf Professional Publishing.

TABLE 2

| | | Case 1 | Case 2 | Case 3 |
|---|---|---|---|---|
| Feedstock throughput | t/h | 200.0 | 200.0 | 200.0 |
| Ni eq. | ppm | 0.1 | 4.0 | 2.9 |
| V eq. | ppm | 0.1 | 12.7 | 9.1 |
| Rate of fresh catalyst addition | t/day | 2.00 | 10.60 | 8.20 |
| Active surface area of the catalyst | m$^2$/g | 147.3 | 146.5 | 146.9 |
| Ni content on the catalyst | ppm | 120 | 1811 | 1698 |
| V content on the catalyst | ppm | 120 | 5660 | 5327 |
| Reaction temperature (RT) | ° C. | 525.0 | 525.0 | 525.0 |
| Catalyst flow rate | t/min | 26.8 | 24.3 | 24.4 |
| C/O ratio | — | 8.03 | 7.29 | 7.32 |
| % coke (delta coke) on the catalyst | wt % | 0.41 | 0.45 | 0.45 |
| Feedstock preheat temperature | ° C. | 416.4 | 208.2 | 273.7 |
| Preheat furnace inlet/outlet temperature difference | ° C. | 208.2 | 0.0 | 65.5 |
| Energy delivered by the feedstock preheat furnace | Mkcal/h | 32.4 | 0.0 | 9.3 |
| Dense phase temperature (= T$_{regen}$) | ° C. | 627.2 | 714.4 | 691.6 |
| Energy to be delivered to the regenerator | Mkcal/h | 0 | 35 | 25 |
| Standard Conversion | wt % | 83.8 | 83.9 | 83.7 |
| H$_2$S | wt % | 0.01 | 0.01 | 0.01 |
| H$_2$ | wt % | 0.00 | 0.01 | 0.01 |
| C1-C2 | wt % | 1.40 | 1.45 | 1.45 |
| C3-C4 | wt % | 23.4 | 23.4 | 23.3 |
| Standard LCN C5-160 | wt % | 44.1 | 44.1 | 44.0 |
| Standard HCN 160-220 | wt % | 11.7 | 11.7 | 11.7 |
| Standard LCO 220-360 | wt % | 11.5 | 11.5 | 11.6 |
| Standard slurry 360$_+$ | wt % | 4.7 | 4.7 | 4.7 |
| Coke | wt % | 3.3 | 3.3 | 3.3 |
| Total | wt % | 100.0 | 100.0 | 100.0 |

TABLE 2-continued

| | | Case 1 | Case 2 | Case 3 |
|---|---|---|---|---|
| Rate of coke injection into the regenerator | kg/h | 0 | 4502 | 3215 |
| Equivalent coke yield | wt % | 3.3 | 5.5 | 4.9 |
| Throughput of air injected into the regenerator | t/h | 91 | 152 | 135 |

Table 2 shows three cases for the operation of an industrial unit.

In the first column entitled "Case 1", or basic case without coke injection, no coke was injected into the regenerator and the preheat temperature of the feedstock injected into the reactor necessary for obtaining 3.3 wt % of coke with a reaction temperature of 525° C. was calculated. In this case, to obtain heat balance of the unit, the feedstock preheat temperature had to be very high and moreover unacceptably high, since above 400° C. the feedstock starts to crack even before it enters the reactor of the unit. In addition, the temperature of the dense phase in the regenerator was barely 627° C., again an unacceptable temperature as it was below the temperature at which the coke deposited on the catalyst contained in the regenerator started to be burnt off.

Two other cases were envisaged for achieving both acceptable preheat temperatures for the feedstock injected into the reactor and acceptable temperatures of the coked catalyst in the dense phase in the regenerator, with an industrial FCC unit operating with a balanced heat balance.

In the configuration of case 2 in Table 2, coke was injected into the regenerator without the ancillary feedstock preheat furnace, the feedstock being preheated only by a series of feedstock/effluent heat exchangers. In this case, the preheat temperature did not exceed 280° C. Therefore, to obtain a sufficiently high temperature of the coked catalyst in the dense phase of the regenerator, typically above 650° C., and to achieve equilibrated heat balance in the unit, it was necessary to supply energy by the combustion of additional coke. In this case, a supply of 35 Mkcal/h to the regenerator then made it possible to obtain a dense phase temperature of 714° C. For such a heat supply, it was then necessary to inject about 4500 kg/h of coke from a coker into the coked catalyst to be regenerated.

The drawback of injecting coke from a coker into the regenerator is the introduction of metals such as Ni and V, known to poison the catalyst, having the effect of deactivating the catalyst. Knowing the rate of injection of coke from a coker into the regenerator and the Ni and V contents, it was then possible to calculate the equivalent Ni and V contents relative to the feedstock deposited on the recirculating catalyst. This exercise allows us to calculate the catalyst make-up necessary for maintaining a satisfactory level of catalytic activity in the cracking unit. To be able to be compared with case 1, the catalyst make-up is adjusted so as to obtain the same level of active area, i.e. about 147 m$^2$/g. Consequently, in comparison with the base case, it may be seen that it was necessary to increase the catalyst make-up from 2 t/day to 10.6 t/day, representing not insignificant additional operating cost of the invention.

To limit this additional operating cost due to the injection of a higher catalyst make-up, the energy delivered to the regenerator by injecting coke from a coker could be reduced by increasing that delivered by the feedstock to the reactor. This is case 3, which consisted in injecting coke into the regenerator while preheating the feedstock with a preheat furnace on the feedstock feed line upstream of the cracking reactor. When the energy delivered to the regenerator was 25

Mkcal/h compared with 35 Mkcal/h, the amount of coke from a coker, to be injected into the regenerator, could be reduced down to 3200 kg/h. By carrying out the same exercise as previously, the fresh catalyst make-up was then reduced to 8.2 t/day, as opposed to 10.6 t/day. When the energy to the regenerator was reduced in this way for a coke yield produced by the equivalent feedstock, to achieve an acceptable heat balance of the unit, it was then necessary to supply energy to the catalyst in the cracking reactor by further preheating the feedstock. In this case, the preheat temperature had to be about 274° C. If the maximum preheat temperature of the feedstock leaving the feedstock/effluent heat exchanger was 208° C., a furnace had to be added, after the heat exchangers, to the feed line for the feedstock to be cracked so as to raise the temperature of the feedstock from 208° C. to 274° C., thereby requiring 9.3 Mkcal/h of heat supplied to the feedstock. In this case, the calculation of the heat balance showed that thermal equilibrium of the unit was thus achieved since the approximately 10 Mkcal/h reduction in energy supplied by adding coke to the regenerator was compensated for by the supply of energy via the preheating of the feedstock using a furnace.

The operating cost savings associated with the reduction in catalyst make-up are therefore offset by the increase in operating costs due to the use of heating fuel in the furnace for heating the feedstock. From an economic standpoint, case 3 is not necessarily better than case 2. Indeed, the sum of the investment costs associated with the installation of a furnace, and for the consumption of a fuel of better quality burnt in said additional furnace, is at least equal if not greater than the cost of the addition of ground coke from a coker, as described in case 2 with an increased fresh catalyst make-up.

In case 3, the temperature in the regenerator was barely above 690° C.: it will be difficult to reduce the volume of coke injected into the regenerator further, and therefore the energy delivered thereby, without running the risk of compromising the efficient operation of the regenerator, i.e. complete combustion of the coke present on the catalyst to be regenerated.

It should also be noted that the yields of cracking products remain equivalent in the three cases envisaged, except for a slight increase in the volume of dry gases for cases 2 and 3 with coke injection, this increase being due to the presence of metals on the catalyst.

Finally, by calculating the equivalent coke yield relative to the feedstock, it is possible to estimate the necessary air throughput into the regenerator for simultaneous combustion of the coke deposited on the catalyst, after cracking of the feedstock in the reactor, and of the coke from a coker added to the regenerator, and to do so for the same excess flue-gas oxygen level.

The invention claimed is:

1. A process for the catalytic cracking of a weakly coking feedstock having a Conradson carbon residue equal to or less than 0.1% by weight and a hydrogen content equal to or greater than 12.7% by weight, implemented in a unit comprising at least a feedstock cracking zone, a separating/stripping zone for separating/stripping effluents from coked catalyst particles and a regeneration zone for regenerating said coked catalyst particles, characterized in that:
   (a) at least a solid carbon material in a fluidized state, having a carbon content equal to or greater than 80% by weight, is dispersed and injected into a dense phase of a fluidized bed of the coked catalyst particles within at least one step of a regeneration zone for regenerating catalyst within the coked catalyst particles, wherein the regeneration zone comprises one or more structured packings for dispersing the coked catalyst particles, wherein a homogeneous dispersion of the solid carbon material in the fluidized state is carried out countercurrently of catalyst circulation, downstream of the one or more structured packings, wherein each of the one or more structured packings is formed by interlacing plates, strips or fins constituting a screen, and wherein the one or more structured packings occupy less than 10% of the flow cross section area of the regeneration zone,
   (b) an amount of the solid carbon material in the fluidized state dispersed within the coked catalyst particles of the fluidized bed is adjusted so as to deliver an additional amount of coke Qc to the coked catalyst so as to satisfy the following equation (I):

$$Qc = Qt - Qi \qquad (I),$$

in which Qi is an initial coke content of the coked catalyst particles after the feedstock has been cracked and Qt or delta coke is a coke content necessary for maintaining a temperature of regenerated catalyst and therefore a heat balance of the process,
   (c) a mixture of coke on the coked catalyst particles and all of the dispersed and injected solid carbon material is burnt in the regeneration zone to produce the regenerated catalyst having a reduced content of carbon material,
   (d) the regenerated catalyst is mixed with the weakly coking feedstock in the feedstock cracking zone to produce the coked catalyst particles and the effluents, and
   (e) the coked catalyst particles are separated from the effluents in the separating/stripping zone, then the coked catalyst particles are sent back to the regeneration zone.

2. The process according to claim 1, characterized in that the solid carbon material is fluidized in a liquid or gaseous effluent not amalgamating with other solid carbon material in the regeneration zone.

3. The process according to one of claim 1, characterized in that Qt is from 0.5 to 1% by weight when the regeneration zone comprises only a single step and from 0.8 to 1.45% by weight for a partial combustion in a first stage of the regeneration zone of a multistage regenerator having at least two regeneration steps.

4. The process according to claim 1, characterized in that the solid carbon material is:
   coke resulting from coking of coal;
   coke from cokers for hydrocarbon effluents having a boiling point above 350° C. chosen from heavy effluent fractions coming from a main cracking reaction, heavy cycle oils with a distillation range typically between 360 and 440° C., and slurries with a distillation range above 360° C.;
   biomass residues coming from conversion of wood and/or cellulose;
   powdered coal dissolved in a fluid hydrocarbon and/or injected by blowing or spraying;
   asphalt-rich fractions coming from deasphalting units;
   non-utilizable waxes coming from liquefaction of coal by an indirect gas-to-liquid (GTL) process or from a Fischer-Tropsch process for converting gas into hydrocarbons; or
   combinations thereof.

5. The process according to claim 1, characterized in that the weakly coking feedstock injected into the feedstock cracking zone comprises one or more of the following feedstocks: purges or bleeds from a hydrocracking unit; feedstocks based on vacuum-distilled gas-oil fractions having a boiling point above 350° C. and having hydrogen contents equal to or greater than 12.7% by weight; vegetable oils; and hydrocarbons having a boiling point below 160° C., wherein these feedstocks are cracked individually or as a mixture in the feedstock cracking zone.

6. The process according to claim 1, characterized in that the dispersion of the solid carbon material in the fluidized state is obtained by means for dispersing said solid carbon material over an entire section of the regeneration zone so that a proportion of catalyst particles over solid carbon material particles is constant in any point of the regeneration zone.

7. The process according to claim 1, characterized in that the dispersion is carried out in the presence of at least one packing placed in a dense phase of a first step of the regeneration zone.

8. The process according to claim 1, characterized in that the solid carbon material in the fluidized state is dispersed over all or part of a height of each dense fluidized bed of the regeneration zone, each dispersion taking place after the dense fluidized bed has been homogenized, wherein the dense fluidized bed is optionally equipped with at least one structured packing.

9. A process for the catalytic cracking of a weakly coking feedstock having a Conradson carbon residue less than or equal to 0.1% by weight and a hydrogen content greater than or equal to 12.7% by weight, the process comprising:
  (a) catalytically cracking a mixture comprising a regenerated catalyst and the weakly coking feedstock to produce a coked catalyst; and
  (b) producing a dispersion of a solid carbon material and injecting the dispersed solid carbon material into a fluidized bed of the coked catalyst, wherein the fluidized bed of the coked catalyst is within a regeneration zone for regenerating the coked catalyst to provide the regenerated catalyst, wherein the solid carbon material has a carbon content greater than or equal to 80% by weight, and wherein the dispersed solid carbon material is injected into a dense phase of the fluidized bed countercurrently of catalyst circulation; and
  (c) burning a mixture of coke on the coked catalyst particles and all of the dispersed and injected solid carbon material in the regeneration zone to produce the regenerated catalyst prior to recycling the regenerated catalyst to the step (a).

10. The process of claim 9, wherein the regeneration zone further comprises one or more structured packings for dispersing the coked catalyst particles, and wherein each of the one or more structured packings comprises interlacing plates, strips or fins constituting a screen.

11. The process of claim 10, wherein the one or more structured packings occupy less than 10% of a flow cross section area of the regeneration zone.

12. The process of claim 11 further comprising injecting the dispersed solid carbon material into the fluidized bed of the coked catalyst downstream of the one or more structured packings.

13. The process of claim 9 further comprising:
  (d) adjusting an amount of the solid carbon material injected into the dense phase of the fluidized bed so as to deliver an additional amount of coke Qc so as to satisfy the following equation (I):

$$Qc = Qt - Qi \tag{I},$$

in which Qi is an initial coke content of the coked catalyst particles produced in the step (a) and Qt is a coke content for maintaining a temperature of the regenerated catalyst.

14. The process of claim 1, wherein the dispersed solid carbon material is injected into the dense phase of the fluidized bed separately from introduction of the coked catalyst thereto.

15. The process of claim 14, wherein the dispersed solid carbon material is injected into the dense phase of the fluidized bed countercurrently from introduction of the coked catalyst thereto.

* * * * *